United States Patent [19]
Ascione et al.

[11] Patent Number: 5,858,334
[45] Date of Patent: *Jan. 12, 1999

[54] ARTIFICIAL TANNING COMPOSITIONS COMPRISING DIHYDROXYACETONE

[75] Inventors: Jean-Marc Ascione, Paris; Delphine Allard, Colombes; Isabelle Hansenne, Paris, all of France

[73] Assignee: Société L'Oréal S.A., Paris, France

[*] Notice: The term of this patent shall not extend beyond the expiration date of Pat. Nos. 5,670,139 and 5,616,331.

[21] Appl. No.: 794,063

[22] Filed: Feb. 4, 1997

Related U.S. Application Data

[63] Continuation of Ser. No. 395,925, Feb. 28, 1995, abandoned.

[30] Foreign Application Priority Data

Feb. 28, 1994 [FR] France .................................. 94 02254

[51] Int. Cl.$^6$ ........................... A61K 7/021; A61K 9/107
[52] U.S. Cl. ........................... 424/59; 424/401; 514/937; 514/938; 514/941
[58] Field of Search ..................... 424/401, 59; 514/937, 514/938, 941

[56] References Cited

U.S. PATENT DOCUMENTS

| | | | |
|---|---|---|---|
| 4,797,273 | 1/1989 | Linn | 424/59 |
| 4,954,332 | 9/1990 | Bissett | 424/59 |
| 5,008,100 | 4/1991 | Zecchino | 424/59 |
| 5,208,028 | 5/1993 | Clement | 424/401 |
| 5,229,104 | 7/1993 | Sottery | 424/59 |

FOREIGN PATENT DOCUMENTS

| | | |
|---|---|---|
| 2597345 | 10/1987 | France . |
| 59-0139310 | 8/1984 | Japan . |
| 93/16683 | 9/1993 | WIPO . |

Primary Examiner—Gollamudi S. Kishore
Attorney, Agent, or Firm—Burns, Doane, Swecker & Mathis, L.L.P.

[57] ABSTRACT

Stable and homogeneous, topically applicable cosmetic compositions well suited for artificially tanning human skin, comprise a storage-stable, ultrafine oil-in-water emulsion, devoid of lipid vesicles, containing an effective artificial tanning amount of dihydroxyacetone, and further wherein the average particle size of the globules comprising the oily phase of the emulsion characteristically ranges from 100 nm to 1,000 nm.

27 Claims, No Drawings

ARTIFICIAL TANNING COMPOSITIONS COMPRISING DIHYDROXYACETONE

This application is a continuation of application Ser. No. 08/395,925 filed Feb. 28, 1995, now abandoned.

BACKGROUND OF THE INVENTION

1. Field of the Invention

The present invention relates to novel cosmetic compositions for topical application, for the artificial tanning of the skin (such compositions sometimes being referred to as self-tanning compositions), to a process for the formulation thereof and also to the use of same for the cosmetic application indicated above.

The present invention more especially relates to artificial suntan compositions having improved activity and which comprise specific oil-in-water emulsions (in a cosmetically acceptable vehicle or carrier) containing dihydroxyacetone as the self-tanning agent.

2. Description of the Prior Art

It is known to this art that dihydroxyacetone, or DHA, is a particularly advantageous compound which is currently employed in cosmetics as an agent for the artificial tanning of the skin. When applied to the skin, especially to the face, it elicits a tanning effect, the appearance of which is similar to that which may result from prolonged exposure to the sun (natural tan) or under a UV lamp. When used as such, moreover, it presents the advantage of totally avoiding the risks of skin reaction which are generally associated with the aforesaid prolonged exposures (erythema, burns, loss of suppleness, appearance of wrinkles, premature aging of the skin, and the like).

For a variety of reasons, especially associated with superior comfort in use (softness, suppleness, ease of application) modern self-tanning compositions are most often produced in the form of an oil-in-water emulsion (i.e., a vehicle comprising an aqueous dispersing continuous phase and an oily dispersed discontinuous phase) into which the dihydroxyacetone has been introduced at various concentrations. The dihydroxyacetone, because of its hydrophilicity, is present in the aqueous phase of the emulsion. In these conventional emulsions, which additionally contain emulsifiers (or surfactants) and optional, conventional cosmetic additives and adjuvants, such as fragrances, dyes or preservatives, the size of the globules constituting the oily liquid phase is generally greater than several microns.

However, one of the disadvantages of the known self-tanning compositions of the above type (O/W emulsion containing DHA) is that the intensity of the coloration obtained on the skin and/or the rapidity with which this coloration develops, is/are ofttimes inadequate.

SUMMARY OF THE INVENTION

Accordingly, a major object of the present invention is the provision of O/W artificial tanning emulsions based on DHA, the self-tanning effectiveness and/or activity on the skin of which is or are conspicuously improved.

Briefly, it has now unexpectedly and surprisingly been found that it is possible to improve the skin-coloring or artificial suntanning power associated with the conventional O/W emulsions of the prior art, based on DHA, by employing specific O/W emulsions, designated "ultrafine" emulsions, the size of the globules constituting the oily phase of which being within well-defined limits. Such ultrafine O/W emulsions are themselves preferably obtained via the so-called "phase inversion" technique more fully described below. All other factors being equal (i.e., at identical chemical compositions and concentrations), it is found that the self-tanning or artificial suntanning compositions according to the invention, by simply adjusting the size of the oily globules to an appropriate value as indicated below, consistently display, in particular in respect of their skin-coloring power, properties which are enhanced relative to an identical self-tanning composition which does not satisfy the criterion indicated above for the size of the oil globules. Moreover, it has surprisingly also been found that, in the compositions of this invention, the DHA exhibits a chemical stability which is markedly increased (less decomposition over time).

DETAILED DESCRIPTION OF BEST MODE AND PREFERRED EMBODIMENTS OF THE INVENTION

More particularly according to the present invention, FR-A-2,597,345, assigned to the assignee hereof, describes the introduction of dihydroxyacetone into aqueous dispersions of multilamellar mesomorphic lipid spherules (niosomes or liposomes), which dispersions may additionally contain, in the dispersing external aqueous phase, a dispersed liquid oily phase. However, as shown by one of the examples given below, even in the instance where this complementary oily phase comprises oily globules whose average size is in accordance with the present invention (see, in particular, Example 4 of the aforesaid '345 application), the advantageous effects and properties associated with the emulsions of the present invention are not provided by such dispersions.

Thus, the present invention features novel cosmetic compositions for the artificial tanning of the skin and which comprise, in a cosmetically acceptable vehicle, carrier or diluent of the oil-in-water emulsion type, dihydroxyacetone as the self-tanning agent, the average particle size of the globules which constitute the oily phase of said emulsion ranging from 100 nm to 1,000 nm, said compositions being devoid, moreover, of lipid vesicles.

The nature of the fatty phase constituting the composition of the emulsions according to the invention is not critical, and may thus comprise any of the compounds which are generally known to this art as being suitable for the formulation of oil-in-water emulsions. In particular, these compounds may be selected, whether singly or in admixture, from among the various fats, oils of vegetable, animal or mineral origin, natural or synthetic waxes, and the like.

Among the oils which may be included in the fatty phase, particularly exemplary thereof are:

(i) mineral oils such as paraffin oil and liquid petrolatum, (ii) oils of vegetable origin such as perhydrosqualene, (iii) oils of vegetable origin such as sweet almond oil, avocado oil, castor oil, olive oil, jojoba oil, sesame oil, groundnut oil, grapeseed oil, rapeseed oil, coconut oil, hazelnut oil, karite butter, palm oil, apricot kernel oil, calophyllum oil, rice bran oil, corn oil, wheatgerm oil, soya oil, sunflower oil, evening primrose oil, safflower oil, passion flower oil and rye oil.

(iv) synthetic oils such as purcellin oil, butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and esters derived from lanolic acid, such as isopropyl lanolate, isocetyl lanolate, and isoparaffins and poly-α-olefins.

Other oils suitable for use in the emulsions according to the invention include the $C_{12}$–$C_{15}$ fatty alcohol benzoates (Finsolv TN marketed Finetex), fatty alcohols such as lauryl alcohol, cetyl alcohol, myristyl alcohol, stearyl alcohol, palmityl alcohol, oleyl alcohol and 2-octyldodecanol, acetylglycerides, octanoates and decanoates of alcohols and polyalcohols, such as those of glycol and glycerol, the ricinoleates of alcohols and polyalcohols such as those of cetyl alcohol, fatty acid triglycerides such as caprylic/capric triglycerides, $C_{10}$–$C_{18}$ saturated fatty acid triglycerides, fluorinated and perfluorinated oils, lanolin, hydrogenated lanolin, acetylated lanolin and, lastly, volatile or nonvolatile silicone oils.

It will of course be appreciated that the fatty phase may also contain one or more conventional lipophilic cosmetic adjuvants or additives, in particular those which are typically formulated into cosmetic artificial suntan compositions.

According to an essential feature of the present invention, the average size of the particles (or globules) of the fatty phase within the dispersing aqueous phase must fall within very specific limits, namely, ranging from 100 nm to 1,000 nm. This average size preferably ranges from 100 nm to 500 nm. Even more preferably, the size distribution of the oily globules is such that the majority of the globules (i.e., at least 90% in numerical terms) have a size which is within the limits indicated above.

In conventional manner, the dispersing aqueous phase may comprise water or a mixture of water and polyhydric alcohol(s) such as, for example, glycerol, propylene glycol and sorbitol, or, alternatively, a mixture of water and water-soluble lower alcohol(s) such as ethanol, isopropanol or butanol (aqueous-alcoholic solution), and it may of course additionally contain conventional water-soluble cosmetic adjuvants and additives.

As indicated above, the dihydroxyacetone is present, by reason of its water-soluble and lipophilic nature, in the aqueous phase of the emulsions according to the invention.

Exemplary traditional cosmetic adjuvants and additives suitable for formulation into the aqueous phase and/or into the fatty phase of the emulsions according to the invention (depending on their water-soluble and/or lipid-soluble character), are, in particular, ionic or nonionic thickeners, softeners, antioxidants, opacifiers, stabilizers, emollients, insect repellants, organic sunscreens which are active in UV-A and/or UV-B, photoprotective inorganic nanopigments and pigments, moisturizers, vitamins, fragrances, preservatives, fillers, sequestering agents, dyes, or any other constituent typically formulated into artificial suntan preparations.

The emulsions according to the invention advantageously contain, in addition, particular surfactants or emulsifiers, the use of which is necessary for preparing and obtaining the ultrafine emulsion, as more fully described below. These can additionally contain specific coemulsifiers, the function of which is to decrease substantially, during the preparation of the emulsion, the amount of surfactants required for producing the emulsion.

For example, the self-tanning or artificial suntan formulations according to the invention typically comprise the following compositions:

(i) aqueous phase: from 50% to 95% by weight, preferably from 70% to 90% by weight, relative to the total weight of the formulation;

(ii) oily phase: from 5% to 50% by weight, preferably from 10% to 30% by weight, relative to the total weight of the formulation;

(iii) dihydroxyacetone: from 0.5% to 10% by weight, preferably from 1% to 7% by weight, relative to the total weight of the formulation; and (iv) (co)emulsifier(s): from 0.5% to 20% by weight, preferably from 2% to 10% by weight, relative to the total weight of the formulation.

A preferred process for formulating the compositions according to the invention will now be more fully described.

As indicated above, this process is based on the technique of preparation of O/W emulsions by phase inversion. The principle of this technique is well known to this art and is described, in particular, in the publication "Phase Inversion Emulsification" by Th. Förster et al, appearing in *Cosmetics & Toiletries,* Vol. 106, December 1991, pp. 49–52. Its principle is thus as follows: an emulsion is prepared (introduction of water into the oil) at a temperature which must be above the phase inversion temperature (or PIT) of the system, namely, the temperature at which the equilibrium or balance between the hydrophilic and lipophilic properties of the emulsifier or emulsifiers employed is attained. At higher temperatures (>PIT), the emulsion is of the water-in-oil type, and, as it cools, at the phase inversion temperature, this emulsion inverts to become an emulsion which is now of the oil-in-water type, having first transferred through a microemulsion state.

According to the invention, DHA must be present in the final O/W ultrafine emulsion. Thus, in a first embodiment of the preparative process according to the invention, the phase inversion of the emulsion is conducted in the presence of DHA (which DHA is preferably present in the initial aqueous phase); in a second embodiment of this process, which is preferred, this DHA is introduced only after the emulsion has been obtained by phase inversion. It is of course possible to utilize both embodiments concurrently.

One of the difficulties in carrying out a process as described above is in the selection of the emulsifying system, which must be suited to the desired result.

The emulsifier or emulsifying systems which must thus be used are those which actually permit stable ultrafine O/W emulsions to be obtained by phase inversion (100 nm<$\Phi_{globules}$<1,000 nm) and in which the DHA is ultimately present only or essentially only in the dispersing aqueous phase.

It has thus been shown that, to this end, the emulsifier systems appropriate to the present invention are nonionic emulsifiers and, more particularly, are polyoxyethylenated and/or polyoxypropylenated fatty alcohols (i.e., compounds prepared by reacting an aliphatic fatty alcohol such as behenyl alcohol or cetyl alcohol, with ethylene oxide or propylene oxide or an ethylene oxide/propylene oxide mixture) and fatty acid esters of polyols, which are optionally polyoxyethylenated and/or polyoxypropylenated (i.e., compounds prepared by reacting a fatty acid, such as stearic acid or oleic acid, with a polyol, for example an alkylene glycol or glycerol or a polyglycerol, optionally in the presence of ethylene oxide or propylene oxide or an ethylene oxide/propylene oxide mixture), or mixtures thereof. Moreover, also preferably, the emulsifier system selected will possess an overall HLB (as is well known, HLB (hydrophilic-lipophilic balance as defined by Griffin; see *J. Soc. Cosm. Chem.,* Vol. 5, pp. 249–256 (1954)), indicating the balance between the hydrophilic character and the lipophilic character of the surfactant) ranging from approximately 9.5 to 11.5, advantageously close to 10, such as to permit a phase inversion to be attained at a temperature of less than 90° C. (PIT<90° C.).

The preparative process according to the invention is described in the examples to follow.

The present invention also features the use of the compositions described above, as, or for the formulation of, cosmetic compositions for the artificial tanning of the skin. The compositions may then be formulated as creams, milks, ointments, cream gels, or, alternatively, as fluid lotions, in particular as vaporizable fluid lotions (the compositions according to the invention exhibiting the additional advantageous property of being fully dilutable in water).

The artificial tanning for the human epidermis according to this invention entails applying to the skin an effective amount of a cosmetic composition as described above, for a period of time sufficient to elicit the desired response.

In order to further illustrate the present invention and the advantages thereof, the following specific examples are given, it being understood that same are intended only as illustrative and in nowise limitative.

EXAMPLE 1

In this example, two emulsions having the same chemical composition based on dihydroxyacetone were prepared and compared, one composition being in accordance with the invention (E1), ultrafine and obtained by phase inversion, the other being comparative (E2), not ultrafine ($\Phi_{globules} > 1$ $\mu$m) and obtained without employing phase inversion.

The chemical compositions (% by weight relative to the overall formulation) of these emulsions were as follows:

| Phase A: | |
|---|---|
| (a) Cetylstearyl alcohol containing 15 mol of ethylene oxide (Mergital CS 15 marketed by Henkel) | 3.3% |
| (b) Glycerol stearate (Tegin 90 marketed by Goldschmidt) | 1.7% |
| (c) Di-n-octyl ether (Cetiol OE marketed by Henkel) | 9% |
| (d) Dioctylcyclohexane (Cetiol S marketed by Henkel) | 9% |
| (e) Cyclomethicone (DC 245 Fluid marketed by Dow Corning) | 4.5% |
| Phase B: | |
| (a) Dihydroxyacetone | 5% |
| (b) Water | 30% |
| Phase C: | |
| (a) Glycerol | 2.5% |
| (b) Water | qs 100% |
| Phase D: | |
| (a) Fragrance | qs |
| (b) Preservatives | qs |

The procedure which was carried out for preparing these two emulsions was as follows: the fatty (A) and aqueous (C) phases were both previously heated to a temperature on the order of 90° C. The aqueous phase (C) was then added to the fatty phase (A) with vigorous stirring of the latter phase using a Moritz turbine stirrer (1,000 rpm). In the case of emulsion E1, this emulsification step was carried out at 80° C., i.e., at a temperature which was above the phase inversion temperature of the system, which in this instance was 72° C. (PIT), whereas in the case of emulsion E2, the emulsification was carried out at 50° C. (i.e., T°C.<PIT). Lastly, first phase (B) and then phase (D) were introduced into the resulting emulsion at about 40° C.

Subsequently, the characteristics relating, on the one hand, to the size of the oil globules (light/optical microscope M×400) and, on the other, to the skin-coloring power or capacity of the two emulsions E1 and E2 thus obtained were then compared. The skin-coloration strength was appraised by means of the following test: the emulsions were applied at a rate of 2 mg/cm$^2$ of skin (squares of approximately 6 cm$^2$) to the forearms of three test subjects (P1, P2 and P3) and the colorimetric deviation of the value L (chromatic coordination of luminance, measured using a Minolta CM 1000 calorimeter) was measured on these forearms before (T0) and after (24 hours) application, such as to determine an absolute value $\Delta$L which provides the intensity of the coloration obtained on the skin after application (the higher the $\Delta$L value, the more intense the coloration):

$$\Delta L = L_{T0} - L_{T24h}$$

The results obtained are reported in Table I below. These results clearly show that emulsion E1 in accordance with the invention artificially suntans the skin, and significantly so, to a coloration which is more intense than that provided by the comparative emulsion E2, 24 hours after application.

TABLE I

| | FORM OF EMULSION | COLORATION ($\Delta$L) | | | |
|---|---|---|---|---|---|
| | | P1 | P2 | P3 | M$^{(1)}$ ($\sigma^{(2)}$) |
| E1 | ULTRAFINE and homogeneous, no oil globules visible by optical microscope ($\Phi < 1$ $\mu$m) | 6.1 | 4.8 | 5.9 | 5.6 (0.7) |
| E2 | coarse emulsion, oil globules visible by optical microscope ($\Phi > 1$ $\mu$m) | 4.1 | 3.8 | 3.8 | 3.9 (0.2) |

$^{(1)}$mean
$^{(2)}$standard deviation

EXAMPLE 2

In this example, the emulsion E1 according to the invention, prepared in Example 1, was compared with a niosome-containing formulation E3 also containing 5% by weight of DHA and prepared in accordance with the procedure of Example 4 of FR-A-2,597,345 (in this instance, the DHA was introduced in the final step of the process).

The chemical composition (% by weight relative to the overall formulation) of this comparative niosome-containing formulation was as follows:

| Dispersed lipid vesicles (niosomes) ($\Phi_{vesicles}$ = approximately 0.5 $\mu$m): | |
|---|---|
| (a) Polyglycerolated cetyl alcohol containing 3 mol of glycerol (Chimexane NL marketed by Chimex) | 3.8% |
| (b) Cholesterol | 3.8% |
| (c) Monosodium stearoyl glutamate | 0.4% |
| Dispersed liquid oily phase ($\Phi_{globules} < 1$ $\mu$m): | |
| (a) Liquid petroleum | 5% |
| (b) Diisopropyl adipate | 12% |
| Dispersing aqueous phase: | |
| (a) Glycerol | 5% |
| (b) Dihydroxyacetone | 5% |
| (c) Hydroxyethylcellulose | 0.5% |
| (d) Fragrance | qs |
| (e) Preservatives | qs |
| (f) Water | qs 100% |

Following the test procedure described in Example 1, the skin-coloring power of each of the two compositions was subsequently evaluated 24 hours after application (T$_{24h}$). The results obtained are reported in Table II below. These results clearly show that the emulsion E1 according to the invention artificially suntans the skin, and significantly so, to a more intense coloration than the comparative emulsion E3, 24 hours after application.

TABLE II

|    | COLORATION (ΔL) | | | |
|----|------|------|------|------------------|
|    | P4   | P5   | P6   | M$^{(1)}$ (σ$^{(2)}$) |
| E1 | 6.6  | 5.4  | 7.5  | 6.5 (1.0)        |
| E3 | 5.6  | 4.4  | 6.0  | 5.3 (0.8)        |

$^{(1)}$mean
$^{(2)}$standard deviation

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic composition adopted for the artificial tanning of human skin, comprising a storage-stable ultrafine oil-in-water emulsion, devoid of lipid vesicles, wherein the average particle size of the globules comprising the oily phase of said emulsion ranges from 100 nm to 1,000 nm, and containing an effective artificial tanning amount of dihydroxyacetone comprised in the aqueous phase of said composition and wherein said oil-in-water emulsion is obtained by phase inversion.

2. The cosmetic artificial tanning composition as defined by claim 1, the average particle size of the globules comprising the oily phase of said emulsion ranging from 100 nm to 500 nm.

3. The cosmetic artificial tanning composition as defined by claim 1, at least 90% of said globules having a particle size ranging from 100 nm to 1,000 nm.

4. The cosmetic artificial tanning composition as defined by claim 2, at least 90% of said globules having a particle size ranging from 100 nm to 500 nm.

5. The cosmetic artificial tanning composition as defined by claim 1, the oily phase of said emulsion comprising a cosmetically acceptable fat, oil, wax, or mixture thereof.

6. The cosmetic artificial tanning composition as defined by claim 1, further comprising at least one emulsifying agent.

7. The cosmetic artificial tanning composition as defined by claim 6, comprising from 0.5% to 20% by weight thereof of said at least one emulsifying agent.

8. The cosmetic artificial tanning composition as defined by claim 7, comprising from 2% to 10% by weight thereof of said at least one emulsifying agent.

9. The cosmetic artificial tanning composition as defined by claim 1, the aqueous phase of said emulsion comprising water, admixture of water and at least one polyhydric alcohol, or admixture of water and at least one water-soluble lower alcohol.

10. The cosmetic artificial tanning composition as defined by claim 1, further comprising at least one cosmetically acceptable adjuvant or additive.

11. The cosmetic artificial tanning composition as defined by claim 10, said at least one adjuvant or additive selected from the group consisting of an ionic or nonionic thickener, softener, antioxidant, opacifier, stabilizer, organic sunscreen, emollient, insect repellent, filler, moisturizer, vitamin, perfume, preservative, sequestering agent, colorant, photoprotective inorganic nanopigment, pigment, and mixtures thereof.

12. The cosmetic artificial tanning composition as defined by claim 1, the aqueous phase of said emulsion comprising from 50% to 95% by weight thereof.

13. The cosmetic artificial tanning composition as defined by claim 12, the aqueous phase of said emulsion comprising from 70% to 90% by weight thereof.

14. The cosmetic artificial tanning composition as defined by claim 12, the oily phase of said emulsion comprising from 5% to 50% by weight thereof.

15. The cosmetic artificial tanning composition as defined by claim 13, the oily phase of said emulsion comprising from 10% to 30% by weight thereof.

16. The cosmetic artificial tanning composition as defined by claim 1, the aqueous phase of said emulsion comprising from 50% to 95% by weight relative to the total weight of the formulation.

17. The cosmetic artificial tanning composition as defined by claim 16, said dihydroxyacetone comprising from 1% to 7% by weight relative to the total weight of the formulation.

18. A process for the preparation of the cosmetic artificial tanning composition as defined by claim 1, comprising (i) emulsifying the aqueous phase into the oil phase thereof, at a temperature above the phase inversion temperature of the medium, (ii) cooling the water-in-oil emulsion thus obtained to a temperature below said phase inversion temperature, thereby converting said water-in-oil emulsion into said ultrafine oil-in-water emulsion, and (iii) introducing said dihydroxyacetone into the medium of emulsion either during the step (i) and/or after the step (ii).

19. The process as defined by claim 18, wherein step (i) is carried out in the presence of an effective emulsifying amount of at least one nonionic surfactant.

20. The process as defined by claim 19, said at least one nonionic surfactant comprising a compound selected from the group consisting of polyoxyethylenated and/or polyoxypropylenated fatty alcohol, a fatty acid ester of a polyol, and mixtures thereof.

21. The process as defined by claim 18, wherein the step (i) medium of emulsion has an overall HLB ranging from about 9.5 to 11.5.

22. The process as defined by claim 21, said overall HLB being approximately 10.

23. The cosmetic artificial tanning composition prepared by the process as defined by claim 18.

24. A method for artificially tanning human skin, comprising topically applying thereto an effective amount of the cosmetic artificial tanning composition as defined by claim 1.

25. The cosmetic artificial tanning composition as defined by claim 1, comprising a cream, gel, ointment, milk or lotion.

26. The process as defined by claim 20, wherein the fatty acid ester of a polyol is polyoxyethylenated and/or polyoxypropylenated.

27. The cosmetic artificial tanning composition as defined by claim 1, wherein said phase inversion comprises (i) emulsifying the aqueous phase into the oil phase thereof, at a temperature above the phase inversion temperature of the medium, (ii) cooling the water-in-oil emulsion thus obtained to a temperature below said phase inversion temperature, thereby converting said water-in-oil emulsion into said ultrafine oil-in-water emulsion, and (iii) introducing said dihydroxyacetone into the medium of emulsion either during the step (i) or after the step (ii), or introducing said dihydroxyacetone both during step (i) and (ii).

* * * * *